United States Patent [19]

Caparrelli et al.

[11] 4,058,120
[45] Nov. 15, 1977

[54] VAPORIZER CAROUSEL FOR ANESTHESIA MACHINE

[75] Inventors: Frederick Caparrelli, Locust Valley, N.Y.; Henry Leong, Kendall Park, N.J.

[73] Assignee: Air Products and Chemicals, Inc., Allentown, Pa.

[21] Appl. No.: 700,861

[22] Filed: June 29, 1976

[51] Int. Cl.$^2$ ............................................. A61M 16/00
[52] U.S. Cl. .................................. 128/188; 128/194; 222/144; 222/325; 261/DIG. 65; 137/614.04; 137/599.1
[58] Field of Search ............... 128/188, 194, 186, 187, 128/209, 210, 197; 222/144, 144.5, 325; 261/DIG. 65, 20, 22, 43; 137/614.04, 599.1

[56] References Cited

U.S. PATENT DOCUMENTS

| 2,118,327 | 5/1938 | Roberts | 128/186 |
| 3,831,599 | 8/1974 | Needham | 128/188 |

FOREIGN PATENT DOCUMENTS

| 255,258 | 11/1912 | Germany | 128/209 |

*Primary Examiner*—Robert W. Michell
*Assistant Examiner*—Henry J. Recla
*Attorney, Agent, or Firm*—Russell L. Brewer; E. Eugene Innis; H. Barry Moyerman

[57] ABSTRACT

This invention relates to an anesthesia dispensing device which comprises a turntable for carrying a plurality of vaporizers having an inlet and outlet port for each vaporizer, and a manifold having a feed port and an exhaust port with a passageway capable of providing communication between the feed port and an external gas supply and a passageway capable of providing communication between the exhaust port and the exterior of the dispensing device. The turntable and manifold are supported for relative rotational and reciprocal movement so that a vaporizer can be rotated into position, engaged and disengaged by simple manipulation.

In a preferred embodiment, at least one directing chamber is disposed in the manifold with an inlet passageway providing communication between the directing chamber and gas supply, and with outlet passageways communicating between each directing chamber and the feed port and exterior of the device, and valve means associated therewith for directing flow either to the feed port or to the exterior. In this way, the unit can dispense anesthetic, a mixture of anesthetics, pure oxygen or a mixture of oxygen and other anesthetic gases as desired.

14 Claims, 10 Drawing Figures

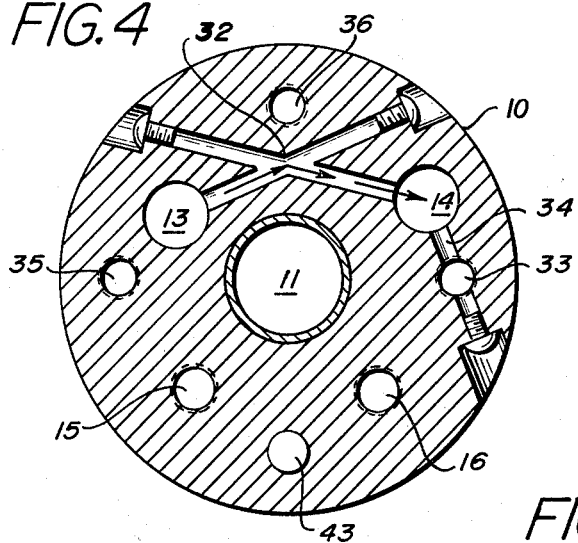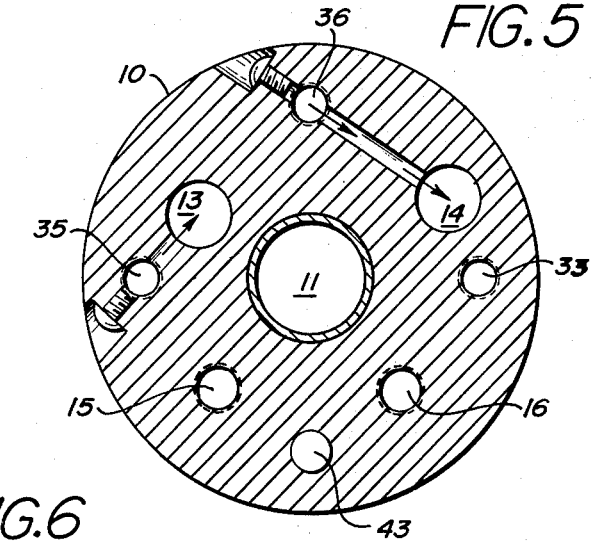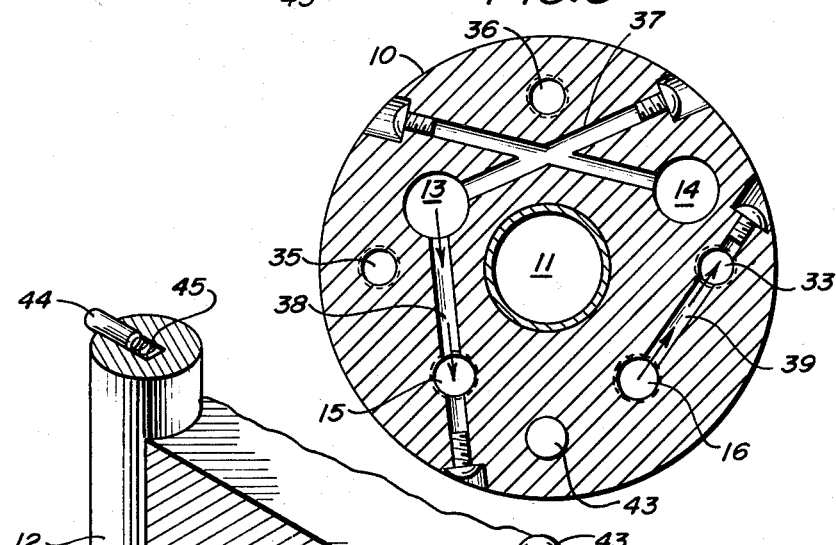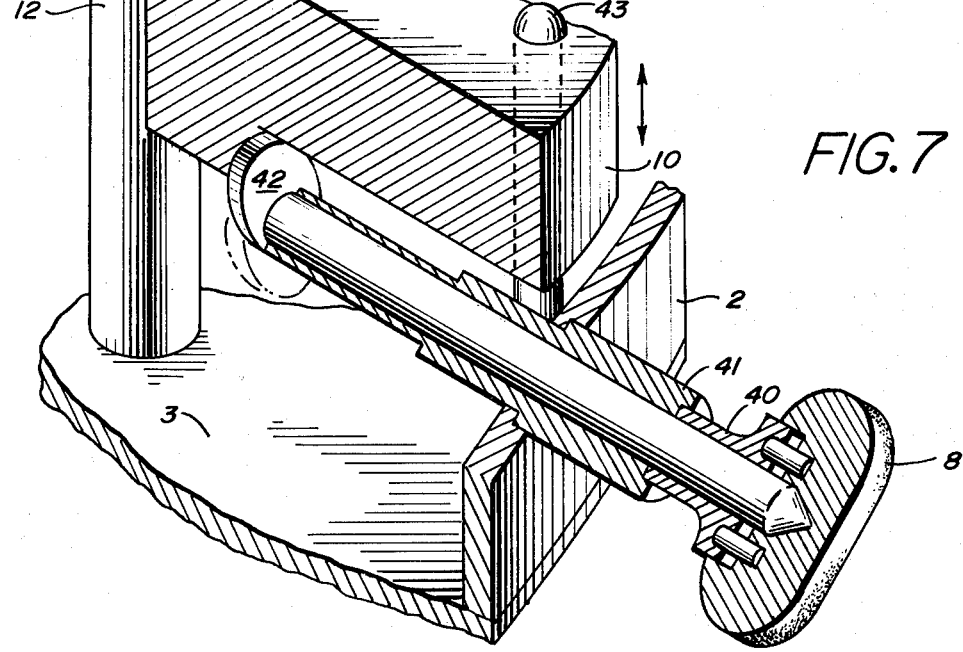

VAPORIZER CAROUSEL FOR ANESTHESIA MACHINE

BACKGROUND OF THE INVENTION

Anesthesia machines utilizing an anesthetic dispensing device for dispensing a plurality of anesthetics from vaporizers and cylinders have been developed and widely utilized by hospitals. These machines permit administration of a single or mixture of anesthetics to a patient in an oxygen or life-supporting atmosphere with convenience to the anesthesiologist and safety to the patient.

The anesthesia machines should also have the capability of dispensing pure oxygen to the patient and the capability of switching back and forth from anesthetic to oxygen. It is further necessary that the anesthesia machine be designed in such a way that the possibility of contamination of gases and human error is minimized. For example, the machine should provide for the complete separation of the anesthesia gases and minimize contamination therebetween. Further, the machine should provide convenience to the anesthesiologist in preparing for subsequent operations and use.

DESCRIPTION OF THE PRIOR ART

Heretofore, in those anesthesia machines carrying a plurality of vaporizers which comprised the anesthesia dispensing device, the vaporizers were mounted on a rack in the machine. The vaporizers were connected in series to a common feed line and exhausted to a common outlet for delivery to the patient. Control of flow to the vaporizers was conducted through a series of selector switches which permitted flow of gas through a preselected vaporizer and prevented flow through other vaporizers. This aspect is shown in U.S. Pat. Nos. 3,703,172 and 3,351,057.

Although anesthesia machines carrying a plurality of vaporizers in series have been acceptable in terms of providing safety to the patient, they have been somewhat cumbersome in design and in operation. Quite often the vaporizers, because of their arrangement on the rack, were difficult to refill and repair for subsequent use. It was also difficult to tell at a glance which vaporizer was in use and there was the opportunity for contamination of the anesthetic.

SUMMARY OF THE INVENTION

This invention relates to an improvement in an anesthesia dispensing device or anesthesia machine. Generally, such machine comprises an oxygen source, a plurality of vaporizers, each capable of containing a different anesthetic, and a means for passing oxygen or other gas through a vaporizer and the breathing circuit for delivery to the patent. The improvement to the anesthesia machine of our invention resides in th dispensing device, i.e., a vaporizer table, carousel or turret which is capable of supporting a plurality of vaporizers, and directing flow to the vaporizer or delivery to the device, i.e. the breathing circuit.

Basically, the vaporizer carousel of our invention comprises two main components. The first of these components is a turntable, carousel or turret designed to carry a plurality of vaporizers each of which is capable of dispensing an anesthetic. The turntable is provided with an inlet port and an outlet port for each vaporizer, i.e. a set. These sets of ports are designed to provide controlled communication with the interior of a vaporizer so that a stream of gas can pass through the inlet port, through the vaporizer and out the outlet port. The second major element of our invention is a manifold or directing block having a feed port and an exhaust port with a first gas inlet passageway for providing communication between a gas source external of the apparatus and the feed port, and a second gas outlet passageway for providing communication between the exhaust port and breathing circuit external of our apparatus. The feed port and exhaust port of the manifold are adapted for sealing registration on engagement with the inlet and outlet ports, respectively, of the turntable.

The turntable and manifold of our vaporizer carousel are supported by any means for rotation relative to each other so as to permit alignment of the feed port with an inlet port of a vaporizer or of a set, while aligning the exhaust port with the outlet port for the same vaporizer or the same set. The turntable and manifold also are supported for relative reciprocal movement so that when the turntable and manifold are moved toward each other sealing engagement of the feed port with an inlet port and the exhaust port with an outlet port of the corresponding vaporizer occurs. Thus, when vaporizers are mounted on our turntable and the manifold and turntable have been moved reciprocally toward each other to effect registration or engagement of the appropriate ports, a continuous passageway is provided from the gas supply external of the apparatus sequentially through the first gas inlet passageway, the feed port, an inlet port, a vaporizer, an outlet port, the exhaust port, the second gas outlet passageway, and the manifold outlet to the exterior of the device of our invention.

Advantages of vaporizer carousel embodiments of this invention include:

a carousel unit which is capable of carrying a plurality of vaporizers on a rotatable turntable which minimizes the amount of space required in an anesthesia machine for carrying such vaporizers;

a carousel unit which provides enhanced convenience of operation to the anesthesiologist because of the ability to move or "dial in" a desired vaporizer for use, or for easy access in the removal or filling of the vaporizer;

a carousel unit which provides, at a glance, information as to which vaporizer is in service;

a carousel unit which provides for enhanced safety to the patient in that only one vaporizer can be engaged in the anesthesia machine at a time;

a carousel unit having a plurality of vaporizers in parallel connection for minimizing contamination in the lines between the vaporizers;

a carousel unit which provides redundant valving so that when the vaporizers are disengaged flow into or out of the vaporizer is impossible;

a carousel unit which can provide a life supporting atmosphere to the patient even when the vaporizers are disengaged;

a carousel unit which provides convenience to the anesthesiologist in that he can prepare several anesthetic formulations and charge them to the vaporizers carried by the carousel and switch from one anesthetic gas to another with a minimum amount of effort; and a carousel unit employing a locking mechanism for preventing accidental engagement or disengagement of a vaporizer.

THE DRAWINGS

FIG. 4 is a cross-sectional view of the manifold of FIG. 3 along the line 4—4 showing the connecting passageways between the third units of the first and second directing chambers and the outlet.

FIG. 5 is a cross-sectional view of the manifold of FIG. 3 along the line 5—5 showing the connecting passageways between second units of the first and second directing chambers.

FIG. 6 is a cross-sectional view of the manifold of FIG. 3 along the line 6—6 showing the connecting passageways between the first units of the first and second directing chambers and the feed port.

FIG. 7 is an isometric view in cutaway showing the actuation mechanism for engaging and disengaging the carousel.

DESCRIPTION OF THE PREFERRED EMBODIMENTS

Figure 1:
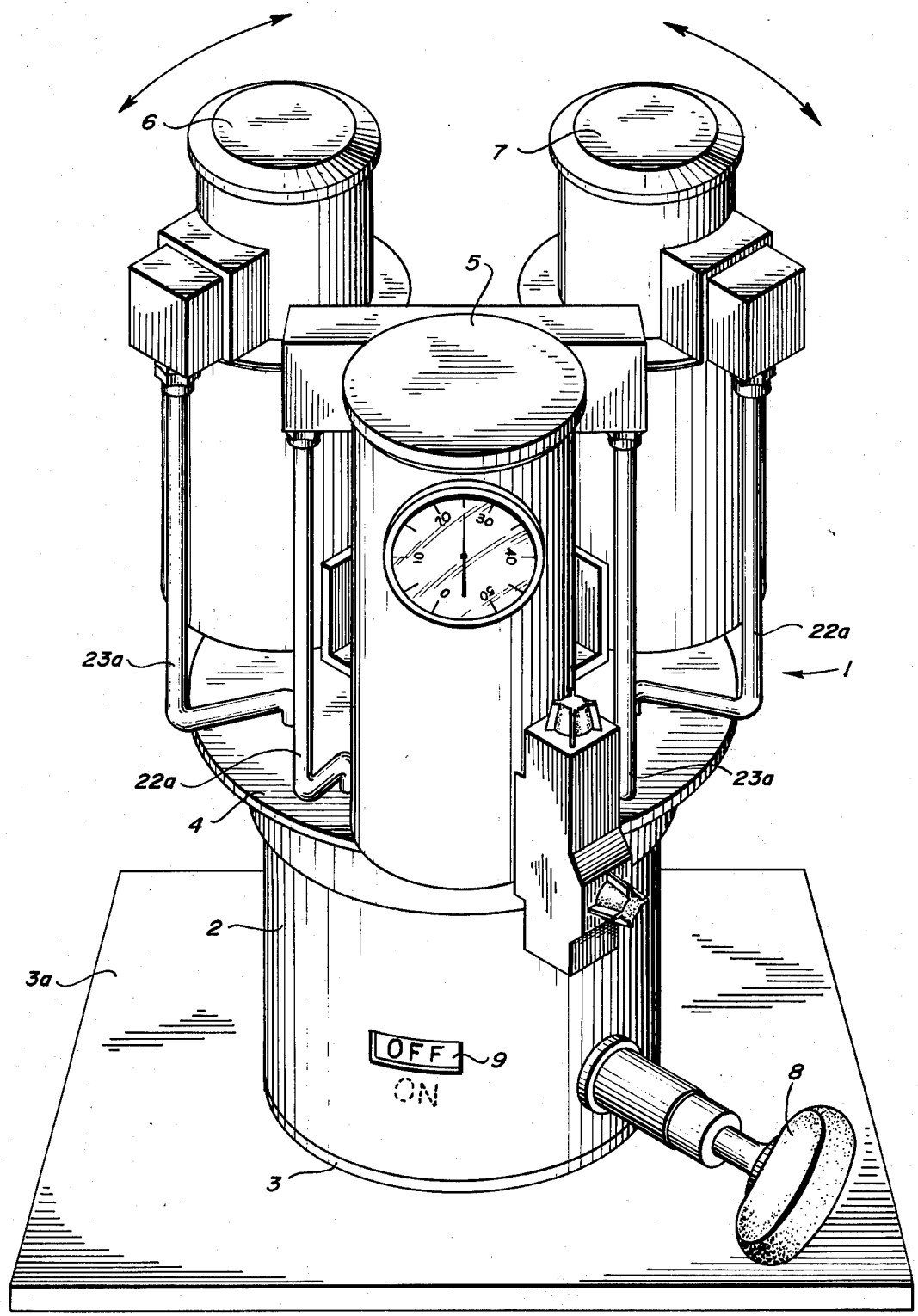
FIG. 1 is an isometric view of the vaporizer carousel unit with the vaporizers attached and the carousel shown in an "OFF" or disengaged position.

In the simplest embodiment, the vaporizer carousel comprises a turntable for carrying a plurality of vaporizers with an inlet and outlet port for each vaporizer carried by the turntable. There is also a manifold which has a feed port, an exhaust port, a passageway to the feed port for providing communication from an external gas source and a passageway from the exhaust port to an outlet from the device. The turntable and manifold are supported for rotational and reciprocal movement vis-a-vis each other to permit engagement and disengagement of the device. Generally, the turntable is supported for relative rotational movement on a tubular housing, and the manifold is supported for axial, reciprocal movement along a shaft disposed inside the tubular housing. To engage a vaporizer, the turntable is rotated, and when a vaporizer is aligned properly, the manifold and turntable are moved toward each other so that the feed port mates with the inlet port, and the outlet port mates with the exhaust port thereby permitting flow from an external source through the feed port, the inlet port, to the vaporizer, through the vaporizer, the outlet port, to the exhaust port, and then to the outlet for discharge to a patient.

This embodiment of our invention can also be provided with its own internal valving such as, simple on-off valves located, for example, at the inlet and outlet ports, and the feed and exhaust ports or both, and it can be operated in conjunction with valving systems external to the vaporizer carousel. When using an external valving system, either with or without internal valves, it is possible to divert a portion of the carrier gas, e.g. oxygen, before introduction into our vaporizer carousel and pass the diverted portion directly to a patient.

Although the above description of the invention is in its simplest sense, a commercial unit which provides additional features is the one shown in the drawings. To facilitate a better understanding of a vaporizer carousel as contemplated on a commercial basis, reference to the drawings is made.

In FIG. 1 there is shown an isometric view of a typical vaporizer carousel contemplated by the invention. Vaporizer carousel 1 comprises a generally cylindrical tubular housing 2, which is preferably supported at one end by a base plate 3 (shown supported on shelf 3a), and a turntable 4. Turntable 4 is rotatably supported on tubular housing 2 and carries a plurality of vaporizers 5, 6 and 7 conventionally used in administering anesthetics. Each of vaporizers 5, 6 and 7 is provided with its own inlet conduit 22a and its own outlet conduit 23a. Typical vaporizers suited for employment are the flow meter controlled vaporizers or Flow Controlled Vaporizers (FCV) and Direct Reading Vaporizers (DRV) sometimes called concentration-calibrated vaporizers. A conventional flow controlled vaporizer is marketed by Foregger Division of Air Products and Chemicals, Inc. under the trademark COPPER KETTLE. Examples of Direct Reading vaporizers which are widely used in administering anesthetics are described in U.S. Pat. Nos. 3,630,438; 3,534,732; and 3,703,172.

Figure 2:
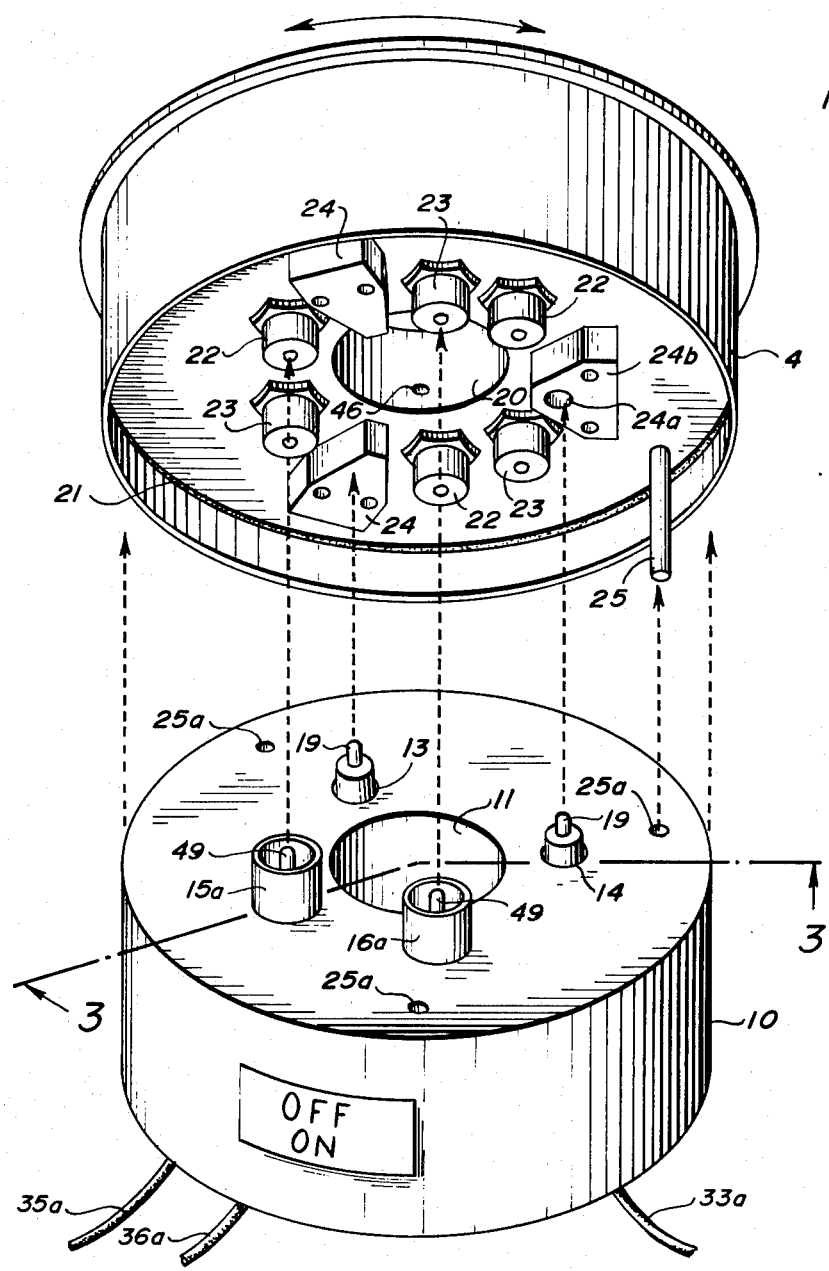
FIG. 2 is an isometric view of the turntable showing the relationship of the valving assemblies between the manifold and turntable.

Greater detail in the construction of the vaporizer carousel 1 is shown in the subsequent drawings beginning with FIG. 2. In that isometric view, emphasis is placed on the turntable 4 and its relationship with manifold 10 for providing the flow directing mechanism from a gas source (not shown) to the vaporizers and to the outlet for delivery to a patient. Particular attention is given in this Figure to the undersurface of turntable 4 and to the upper surface of manifold 10 illustrating the manner in which the various portions of these two members cooperate when the two pieces are properly aligned and registered.

Manifold 10 is a generally circular block having an aperture 11 for permitting coaxial, slidable movement along shaft 12 (shown in FIG. 3), with shaft 12 disposed coaxially within tubular housing 2. Shown on the upper surface of manifold 10 are the upper openings of first directing chamber 13 and second directing chamber 14. Positioned within the first and second directing chambers 13 and 14 and extending upwardly therefrom are push rods 19. Also shown extending upwardly from the upper surface of manifold 10 are feed port collar 15a and exhaust port collar 16a within each of which is positioned a push rod 49. Finally, spaced about manifold 10 are three alignment pin holes 25A. Extending from the underside of manifold 10 there are shown manifold outlet line 33a and inlet lines 35a and 36a. The connection of each of these three lines, as well as its function, will be explained more fully in the description of FIGS. 3 through 6 below.

Referring now to the undersurface of turntable 4, there will be seen three pairs (sets) of ports with each pair comprising an inlet port 22 and an outlet port 23. Each of the inlet ports 22 communicates with the inlet conduit 22a of a particular vaporizer, while each of the outlet ports 23 communicates with the outlet conduit 23a associated with the same vaporizer. Located on the undersurface of turntable 4 and positioned between the inlet and outlet ports 22 and 23 of each set is a valve actuating block 24 and one of these blocks, designated 24b, is provided with a push rod receiving hole 24a. Also extending downwardly from the undersurface of turntable 4 is an alignment pin 25 adapted to be received into one of the alignment pin holes 25a in manifold 10. Alignment pin 25 functions to prevent the coming together of the confronting upper surface of manifold 10 and the lower surface of turntable 4 until alignment pin 25 is capable of being received into one of the alignment pin holes 25a at which time alignment pin 25 and alignment pin hole 25a cooperate so as to insure alignment of the push rods 19 with a combination of two valve actuating blocks 24 or 24b and feed port collar 15a with an inlet port 22 and exhaust port collar 16a with an outlet port 23, which inlet and outlet ports are associated with the same vaporizer. Alignment pin 25 and alignment hole 25a further cooperate to permit relative movement of turntable 4 and manifold 10 toward each other to effect registration, engagement and cooperation between the above-recited aligned members on turntable 4 and manifold 10.

Figure 3:
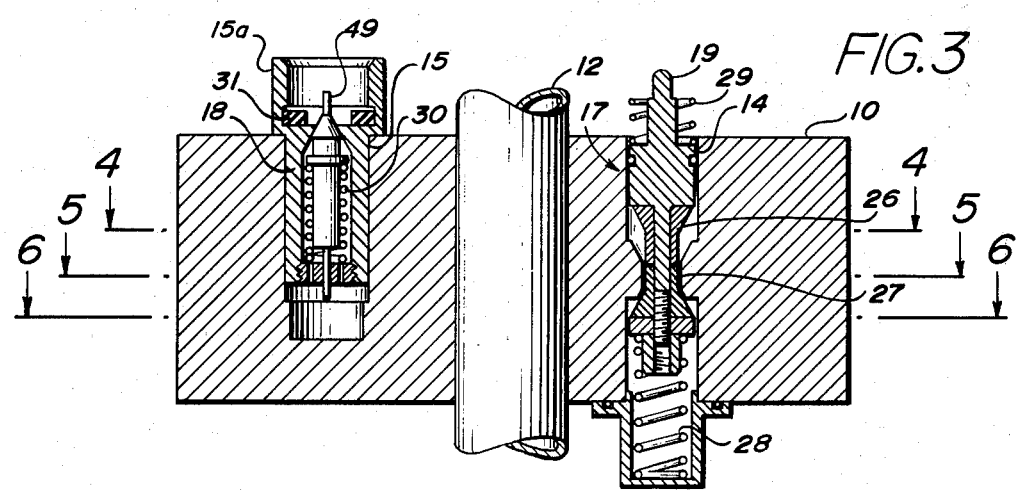
FIG. 3 is a cross-sectional view of the manifold shown in FIG. 2 along the line 3—3 showing a typical plunger valve assembly and a poppet valve assembly.

FIG. 3, which illustrates in greater detail the construction of valving devices in second directing chamber 14 and feed port 15. The same type valve device is present in both the first and second directing chambers 13 and 14, respectively. Similarly, the same type valving device is present in feed port 15 and exhaust port 16, as well as inlet ports 22 and outlet ports 23.

Having explained the general structure of turntable 4 and manifold 10 in FIG. 2, analysis of FIG. 3 provides a description of the valving assemblies, namely the plunger valve assemblies 17 which are present in first directing chamber 13 and second directing chamber 14 and which direct flow to feed port 15 or manifold outlet 33 and the poppet valve assemblies 18 which are present in feed port 15 and exhaust port 16 and which direct flow therefrom. Also, poppet valve assemblies 18 generally are included in all of the inlet ports 22 and outlet ports 23 for controlling flow into and out of these ports, but such valve assemblies are optional.

More particularly, plunger valve assemblies 17 comprise, as viewed in FIG. 3, an upper valve 26 and a lower valve 27. These valves are coupled together so that they move in unison, thus when one valve is closed the other is open. Control of these valves is effected by means of push rods 19 which, when forced downwardly by valve actuating block 24, push against upper valve 26, which in turn pushes against lower valve 27 for effecting closing of upper valve 26 and opening of lower valve 27. Plunger valve assemblies 17 in the first and second directing chambers 13 and 14 have springs 28 located at the bottom and springs 29 located at the top. The bottom springs 28 urge or bias the lower valve 27 to a normally closed position, (flow is prohibited to feed port 15) and the upper valve 26 to a normally open position (flow is permitted to manifold outlet 33). The upper springs 29 act as a cushion between the plates 24 and push rods 19 when manifold 10 is in engaged relationship with turntable 4, i.e. raised in tubular housing 2.

Poppet valve assemblies 18 as viewed in FIG. 3 are present in feed port 15, and exhaust port 16 primarily to prevent flow of gas from manifold 10 to the atmosphere. Poppet valve assemblies identical to those shown in feed port 15 and exhaust port 16 are present in each inlet port 22 and each outlet port 23 to prevent flow of anesthetic from either the inlet or outlet port of a vaporizer when the unit is disengaged. These poppet valve assembles not only prevent contamination of the anesthetic in the vaporizer but prevent pollution of the operating room.

Basically, poppet valves 18 assemblies as shown are simple on-off valves which are biased to a normally closed position by spring 30. When the manifold 10 and turntable 4 are engaged, the valves are opened by push rods 49 thereby permitting gas to flow from feed port 15 to inlet port 22, through preselected vaporizers 5, 6 and 7 back through outlet port 23 to the exhaust port 16, and then to manifold outlet 33. Leakage of gas between feed port 15 and inlet port 22 and outlet port 23 and exhaust port 16 is prevented by sealing surface 31 which seals against the inlet and outlet port surfaces when the ports are registered.

FIGS. 4, 5 and 6 are cross-sectional views of manifold 10 showing the division of the first and second directing chambers 13 and 14 into three units and the interconnecting passageways between these units and feed port 15, exhaust port 16, manifold outlet 33 and gas inlet passageways 35 and 36. More particularly, with respect to FIG. 4, the cross section gives a view of passageways in the third unit or the upper unit. FIG. 5 provides a view of the passageways in the second unit or the middle unit, and FIG. 6 provides a view of the passageways in the first unit or the lower unit.

With respect to FIG. 4, the third units of first directing chamber 13 and second directing chamber 14 are connected via passageway 32 and manifold outlet 33 is connected to second directing chamber 14 via passageway 34. Manifold outlet 33 is connected to outlet line 33a as shown in FIG. 2 for permitting delivery to the patient.

With respect to FIG. 5, the second units or middle units of first directing chamber 13 and second directing chamber 14 are connected to gas inlet passageways 35 and 36 respectively. Inlet Lines 35a and 36a as shown in FIG. 2 are connected to a gas source (not shown) and to gas inlet passageways 35 and 36, thereby permitting inroduction of gas to the middle units of chambers 13 and 14.

With respect to FIG. 6, the first unit of first directing chamber 13 is connected to the first unit of second directing chamber 14 via passageway 37 and to feed port 15 via passageway 38. Passageway 39 connects exhaust port 16 to manifold outlet 33. Hence, gas will flow from feed port 15 through the vaporizer in the circuit to exhaust port 16, then to manifold outlet 33 via passageway 29 and then to the patient.

Once understanding the basic structure and valving assemblies of the vaporizer carousel, the actuating mechanism for alignment and effecting engagement can be considered. Referring to FIG. 7, the actuating mechanism can be described as a handle 8 coupled to a latching mechanism comprising a trigger section 40 and lock 41. When trigger section 40 is squeezed, it is disengaged from lock 41 which then permits handle 8 to be rotated. When handle 8 is rotated, cam 42 rotates and presses against manifold 10 causing it to move upwardly in said tubular housing for effecting engagement and registration. When handle 8 is rotated 180°, cam 42 is moved to a lowered position thereby permitting manifold 10 to drop and to effect disengagement. Window 9 as shown in FIG. 1 readily permits the anesthesiologist to determine whether the unit is engaged "ON" or disengaged "OFF". During raising or lowering of manifold 10, the rotational movement is prevented about the horizontal axis by virtue of indexing pin 43 secured to base 3.

A preselected vaporizer carried by turntable 4 is aligned for engagement into the system by a roller bearing-detent mechanism. More particularly, a roller bearing 44 which is urged radially outwardly by spring 45 from shaft 12 rides about the periphery of aperture 20 in turntable 2. When the turntable is rotated and roller bearing 44 contacts detent 46 (FIG. 2), a click is heard and felt and the anesthesiologist knows that particular vaporizer is substantially in alignment. Precise alignment and securing of turntable 4 against manifold 10 is achieved by virtue of alignment pin 25 in turntable 4 engaging one of the holes 25a. The insertion of alignment pin 25 into one of the holes 25a also prevents damage to the poppet valve assemblies and insures complete registration of the feed and exhaust port with the inlet and outlet port.

Figure 8:
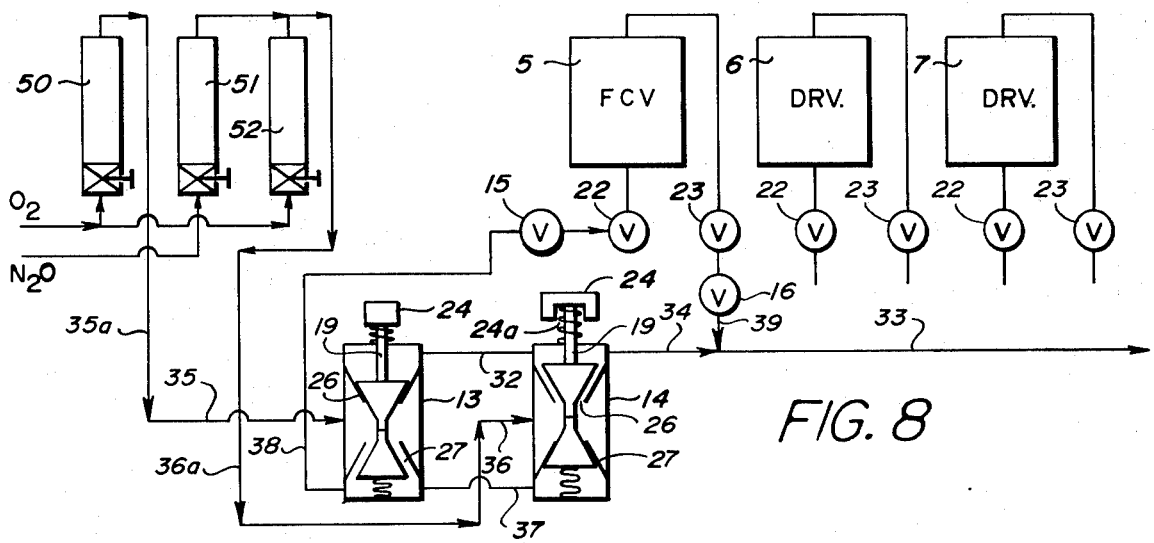
FIG. 8 is a flow diagram utilizing a Flow Controlled Vaporizer (FCV) where part of the patient's oxygen requirements are passed to the FCV.

FIG. 8 shows a typical flow pattern established upon registration of turntable 4 and manifold 10 and employing a flow controlled vaporizer (FCV) which is suited for dispensing a number of anesthetics such as diethyl ether, chloroform, halothane, and methoxyfluorane. More particularly in the anesthesia machine, oxygen and nitrous oxide or other anesthetic cylinder gases are supplied from a gas source (not shown) to rotameters 50, 51 and 52. The output from rotameter 50 communicates via inlet line 35a and inlet passageway 35 to the middle unit of first directing chamber 13 and the combined output from rotameters 51 and 52 communicates via line 36a and inlet passageway 35 to the inlet, i.e. the middle unit of second directing chamber 14. With the vaporizer carousel unit engaged, valve actuating block 24 pushes downwardly on push rod 19 thereby forcing the upper valve 26 and lower valve 27 downwardly in first directing chamber 13. This action causes upper valve 26 to close the upper unit (thereby preventing flow directly to manifold outlet 33) and lower valve 27 to open (thereby permitting flow to feed port 15 via passageway 38). Valve actuating block 24, which has an aperture 24a, permits plunger valve assembly 17 in second directing chamber 14 to remain in its normal position, i.e. lower valve 27 remaining in a closed position and upper valve 26 in an open position. Due to the presence of poppet valve assemblies 18 in each of the feed port 15, exhaust port 16, inlet ports 22 and outlet ports 23, such ports are shown as valves in FIGS. 8, 9 and 10, and designated by the reference numbers 15, 16, 22 and 23.

When oxygen is directed through rotameter 50, the gas passes through line 35a and passageway 35 into the inlet, i.e. the second unit of first directing chamber 13, and out the first unit via passageway 38 to feed port 15. Since feed port 15 is registered with an inlet port 22 and exhaust port 16 is registered with an outlet port 23, the poppet valve assemblies 18 in each of these ports are open thereby permitting flow to feed port 15, to inlet port 22 through the vaporizer back through outlet port 23 to exhaust port 16, to passageway 39, to manifold outlet 33 and then to line 33a for delivery to the patient. Meanwhile, other anesthetic gases, e.g. N$_2$O, can pass through rotameter 51 and oxygen can pass through rotameter 52, through line 36a to the inlet, i.e. the middle unit of second directing chamber 14, and out the third or upper unit via passageway 34 to outlet 33 and ultimately on to the patient. At that point the oxygen stream which passes through the flow controlled vaporizer 5, i.e. the stream of passageway 39, and the oxygen or anesthetic-oxygen stream from second directing chamber 14, i.e. the stream of passageway 34, are combined in manifold outlet passageway 33 for mixing and forming a homogeneous anesthetizing atmosphere for delivery to the patient by conventional manner.

Figure 9:
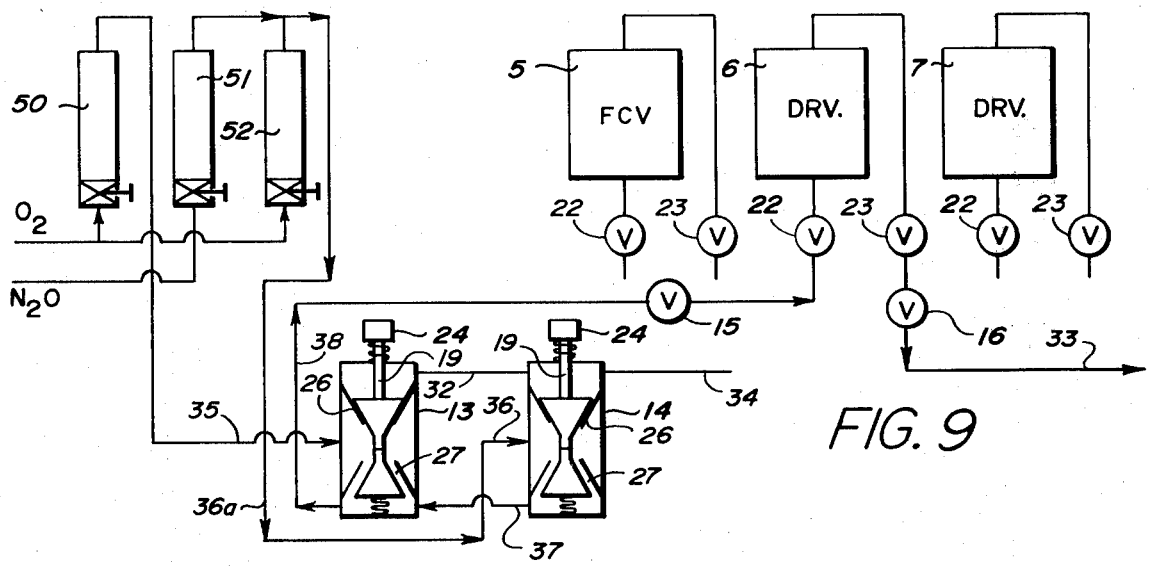
FIG. 9 is a diagram of a flow diagram pattern utilizing a Direct Reading Vaporizer (DRV) wherein all of the patient's oxygen requirements are passed to the vaporizer, and the vaporizer meters the flow.

FIG. 9 is typical view of a flow diagram with a single Direct Reading Vaporizer engaged. Typically, all of the patients' oxygen requirements are passed through the Direct Reading Vaporizer as the vaporizer itself provides for the desired amount of anesthetic and oxygen to be delivered to the patient. Such vaporizers are used for administering anesthetics, such as, for example, halothane. In this system, with the manifold engaged, valve actuating blocks 24 force push rods 19 downwardly thereby closing the third or upper units and opening lower valve 27 in the first or lower units of first directing chamber 13 and second directing chamber 14. Thus, all gases flowing through rotameters 50, 51 and 52 pass to the second or middle units of first and second directing chambers 13 and 14, out the first or lower units via passageways 37 and 38, through the feed port 15, through the inlet port 22 of the Direct Reading Vaporizer and then to outlet port 23, exhaust port 16, passageway 39 and manifold outlet 33 for subsequent delivery to a patient.

Figure 10:
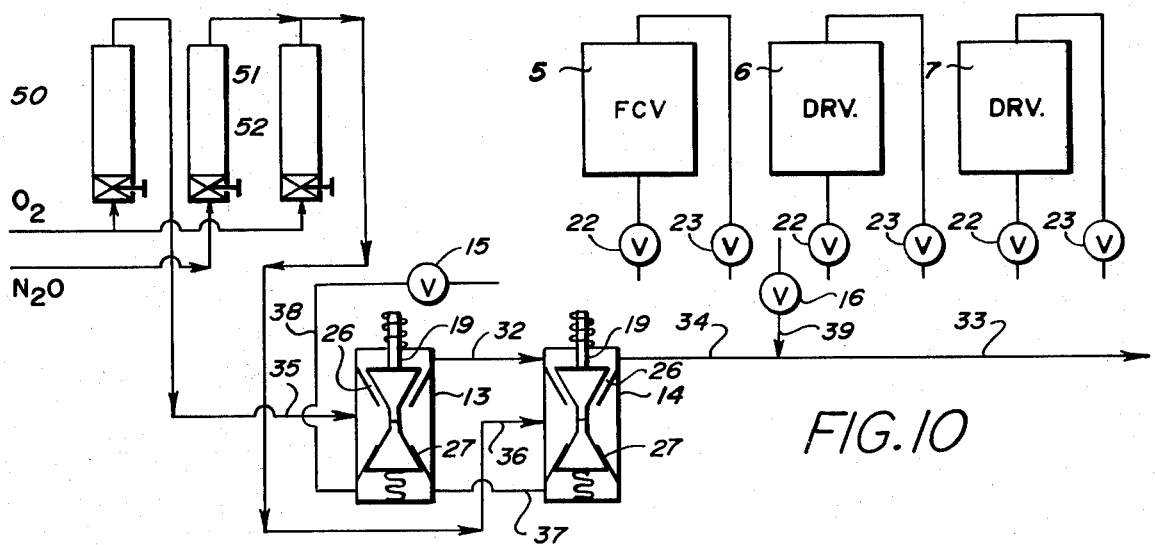
FIG. 10 is a flow diagram when the carousel unit is disengaged and is supplying continuous oxygen or anesthetic from a compressed source, e.g. $N_2O$ or $CO_2$.

FIG. 10 shows the flow pattern when the vaporizer carousel is disengaged and the unit is delivering total oxygen or a mixture of anesthetic gas from a compressed source and oxygen. With manifold 10 lowered, plunger valve assemblies 17 in first and second directing chambers 13 and 14 are in their normal position i.e., lower valves 27 are in the closed position thereby preventing flow of gas to feed port 15 and upper valves 26 are in their normally open position thereby permitting flow via passageways 32 and 34 to manifold outlet 33 and then to the patient. Thus, all of the vaporizers are out of the circuit and there can be no contamination of the patient's oxygen supply.

These flow patterns show that it is possible to direct a part or all of the gas flow to a single vaporizer depending on the requirements. They also show the cooperation of the plunger valves and the poppet valves in providing a redundant valving system for enhanced insurance that of the patient's oxygen as read from the rotameters is in fact delivered to the patient and is not contaminated by anesthetic.

It is understood that variations in the operation of the vaporizer carousel can be achieved without detracting from the spirit of the invention. For example, it is possible to arrange the vaporizer carousel in such a way that the turntable is supported for reciprocal movement relative to the manifold for engagement and disengagement therewith, and the manifold is supported for rotational movement. It is possible to alter the valving means in the first and second directing chambers and feed port, exhaust port, inlet port and outlet port and to alter the control techniques to achieve the same type of flow. In this regard, the terms plunger valves and poppet valves are used for convenience but it is understood that other kinds of valve means and control means that will provide the same result can be used and the terms are inclusive of these valve means. Also, for convenience, the upper outlet passageway in the first directing chamber is connected to the upper unit of the second directing and the outlet passageway is vice versa in the lower units of the first and second directing chamber. Although graphically this may appear to be two inlets, the function is that of an outlet for these directing chambers.

What is claimed is

1. An improved anesthesia dispensing machine comprising:
   a. a directing block member having a feed port, and an exhaust port including first means for providing fluid communication between an external gas supply and the feed port, and second means for providing fluid communication between the exhaust port and the exterior of the dispensing machine;
   b. a turntable having means for mounting a plurality of anesthesia vaporizers thereon, the turntable having a plurality of sets of an inlet port and an outlet port, with each set of an inlet port and an outlet port adapted for communication with the interior of a single vaporizer, said turntable and said block mounted for movement relative to each other;
   c. means for effecting rotational and reciprocal movement between the turntable and the directing block member for effecting engagement of the feed port with an inlet port and an outlet port with the exhaust port for a preselected vaporizer;
   d. means for sealing said feed port against said inlet port and said exhaust port against said outlet port when engaged;
   e. valve means in each of said inlet ports, said outlet port, said feed port and said exhaust port, the valve means normally being in a closed position and each of said valve means being separately actuable thus permitting communication through the respective ports when the ports are in sealing engagement with each other;
   whereby sealingly engaging a set of inlet and outlet ports with the feed and exhaust ports thus providing communication from an external gas supply to the feedport, through the juxtaposed inlet port, a vaporizer, an outlet port, and through the juxtaposed exhaust port, to the exterior of the dispensing machine.

2. The machine of claim 1 wherein the gas inlet passageway is provided with means defining a directing chamber intermediate the ends of the gas inlet passageway with one end of the gas inlet passageway providing communication between the external gas supply and the directing chamber and the other end of the gas inlet passageway providing communication between the directing chamber and the feed port, other means are provided defining a connecting passageway providing communication between the directing chamber and the exterior of the machine, the directing chamber being provided with valve means normally being in a first position permitting communication from the external gas supply, through the chamber, to the connecting passageway and the exterior of the machine, while preventing communication from the chamber through the other end of the gas inlet passageway to the feed port, and being actuable to a second position permitting communication from the external gas supply, through the chamber, to the other end of the gas inlet passageway and the feed port, while preventing communication from the chamber, through the connecting passageway to the exterior of the machine and control means for actuating the directing chamber valve.

3. The machine of claim 2 wherein the directing block member is provided with a plurality of means each defining an inlet passageway having a directing chamber intermediate the ends thereof and each chamber being provided with separate valve means and separate connecting passageways, and wherein a plurality of separate control means are provided for separately and selectively actuating directing chamber valves.

4. An anesthesia dispensing machine as in claim 1, in combination with an anesthesia machine comprising an oxygen source connected to said feed port, a plurality of vaporizers mounted on said turntable and containing a liquid anesthetic and including means for producing an anesthetizing atmosphere by mixing said anesthetic with oxygen, and a breathing circuit connected to said exhaust port for delivery of the resulting anesthetizing gas-oxygen mixture to the patient and thereby providing enhanced convenience to the anesthesiologist and safety to the patient.

5. A vaporizer carousel anesthesia dispensing device capable of providing a carrier gas atmosphere when in a first mode, and an anesthetizing quantity of anesthetic when in a second mode, which comprises:
   a turntable having means for mounting a plurality of vaporizers and rotatable about its axis, the turntable having a plurality of sets of an inlet port and an outlet port with each set of an inlet port and an outlet port adapted for providing communication with the interior of a single vaporizer;
   a manifold containing means defining first and second directing chambers, each of said chambers having an inlet and at least first and second outlets spaced apart from each other, a feed port, an exhaust port, a manifold outlet, a first passageway providing communication from the exhaust port to the first outlets in the first and second directing chambers and to the manifold outlet, a second passageway providing communication from the feed port to the second outlets in the first and second directing chambers;
   means for providing fluid communication to the inlets of the directing chambers;
   alignment means for effecting registration of the feed port and the exhaust port with the inlet port and the outlet port, for providing communication with the interior of a preselected vaporizer;
   means for effecting relative reciprocal and rotational movement between the manifold and the turntable from a first mode where the feed and exhaust ports are not in sealing engagement to a second mode where the feed and exhaust ports are in sealing engagement with the inlet and outlet ports, respectively, of a set;
   separate directing valve means disposed in each of the first and second directing chambers, each valve means having a first position permitting communication from the inlet to the chamber to the first outlet from such chamber, while preventing communication from the inlet to the chamber to the second outlet from such chamber and a second position permitting communication from the inlet to the chamber to the second outlet from such chamber, while preventing communication from the inlet to the chamber to the first outlet from such chamber, the valve means normally being in the first position, and each valve means being separately actuable to the second position;
   control means for selectively and separately actuating the directing valve means in a predetermined manner when the feed and exhaust ports are sealingly engaged with the inlet and outlet port; of a preselected vaporizer and valve means associated with the inlet ports and with the outlet ports, the inlet and outlet port valve means normally being in a first closed position preventing communication through the port associated with the valve means and separately actuable to a second position permitting communication through the port associated with the valve means upon sealing engagement of the inlet port and the outlet port of a set with the feed port and exhaust port, respectively;

whereby when registration and sealing engagement of the feed port with an inlet port of a set and registration and sealing engagement of the exhaust port with the outlet port of the set occurs in the second mode, the valve means associated with the set of an inlet valve and an outlet valve are actuated to the second position and at least one of the directing valve means is actuated to its second position thereby permitting gas to flow from the external carrier gas supply and at least one of the inlets in said first and second directing chambers to said feed port, said inlet port, through a vaporizer, said outlet port, said exhaust port, and then to said manifold outlet, and when in the first mode and the feed and exhaust ports are not sealingly engaged with a set of inlet and outlet ports, all valve means are in the first position directing flow from both inlets in the first and second directing chambers to the manifold outlet.

6. The vaporizer carousel of claim 5 comprising a tubular housing and a shaft, coaxially disposed in said housing, said housing adapted for rotatably supporting the turntable.

7. The vaporizer carousel of claim 6 wherein said directing block is supported in said tubular housing and disposed about the shaft for reciprocal movement thereon.

8. The vaporizer carousel of claim 7 wherein said turntable is rotatably supported on an end of the tubular housing.

9. The vaporizer carousel of claim 7 wherein an indexing pin is employed for continuous engagement with said manifold to prevent rotation thereof but permitting slidable movement in said tubular housing.

10. The vaporizer carousel of claim 7 wherein a handle is disposed in said tubular housing, said handle carries a cam for effecting reciprocal movement of said manifold in said tubular housing.

11. The vaporizer carousel of claim 5 wherein each of the first and second directing chambers are divided into three separate units; a first unit, a second unit, and a third unit with the inlet located in said second units of said first and second directing chambers with the second outlets located in said first units of said first and second directing chambers communicating with the feed port and with the first outlets located in said third units of said first and second directing chambers communicating with the exterior of the machine.

12. The vaporizer carousel of claim 11 having a passageway communicating with the second outlet in said first unit of said first directing chamber, the feed port, and with the second outlet in said first unit of said second directing chamber, and another passageway communicating with the first outlet in said third unit of said first directing chamber, with said first outlet in the third unit of said second directing chamber and with said exhaust port and the exterior of the machine.

13. The vaporizer carousel of claim 12 wherein said valve means comprise plunger valves disposed in said first units and in said third units of said first and second directing chambers for permitting flow control to either the feed port or to the exterior of the machine.

14. The vaporizer carousel of claim 13 wherein push rods are employed for effecting appropriate controlled movement of the plunger valves in said first and second directing chambers.

* * * * *